United States Patent [19]

Nakamura et al.

[11] Patent Number: 5,449,661
[45] Date of Patent: Sep. 12, 1995

[54] ANGIOTENSIN CONVERTING ENZYME INHIBITOR AND METHOD FOR PREPARING SAME

[75] Inventors: Yasunori Nakamura, Yokohama; Toshiaki Takano, Kawasaki, both of Japan

[73] Assignee: The Calpis Food Industry Co., Ltd., Tokyo, Japan

[21] Appl. No.: 384,618

[22] Filed: Feb. 6, 1995

Related U.S. Application Data

[63] Continuation of Ser. No. 90,530, Jul. 12, 1993, abandoned.

[30] Foreign Application Priority Data

Jul. 23, 1992 [JP] Japan ................... 4-197239

[51] Int. Cl.$^6$ .............................................. A61K 38/00
[52] U.S. Cl. ......................................... 514/15; 514/16; 514/17; 514/18
[58] Field of Search ......................... 514/15–18

[56] References Cited

U.S. PATENT DOCUMENTS 4,810,779  3/1989  Caciagli et al. ................. 530/328

OTHER PUBLICATIONS

Bolis et al, J. Med. Chem. vol. 30 p. 317 (1987).
Rapaka et al Biopolymers vol. 15 pp. 317–324 (1976).

*Primary Examiner*—Howard E. Schain
*Assistant Examiner*—Sheela J. Huff
*Attorney, Agent, or Firm*—Darby & Darby

[57] ABSTRACT

An angiotensin converting enzyme inhibitor contains as an effective constituent Val-Pro-Pro and contains 3 to 10 amino acid residues. A method for producing the aforementioned angiotensin converting enzyme inhibitor involves fermenting a foodstuff material containing Val-Pro-Pro as a constituent component with lactic acid bacteria.

2 Claims, No Drawings

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 3 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:1:

Val  Pro  Pro
    1

( 2 ) INFORMATION FOR SEQ ID NO:2:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

Val  Val  Pro  Pro
    1

( 2 ) INFORMATION FOR SEQ ID NO:3:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

Val  Val  Val  Pro  Pro
    1                        5

( 2 ) INFORMATION FOR SEQ ID NO:4:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

Pro  Val  Val  Val  Pro  Pro
    1                        5

( 2 ) INFORMATION FOR SEQ ID NO:5:

( i ) SEQUENCE CHARACTERISTICS:
    ( A ) LENGTH: 10 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:5:

Leu Thr Gln Thr Pro Val Val Val Pro Pro
1               5                   10

( 2 ) INFORMATION FOR SEQ ID NO:6:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

Leu Val Pro Pro
    1

( 2 ) INFORMATION FOR SEQ ID NO:7:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

Phe Leu Val Pro Pro
    1               5

( 2 ) INFORMATION FOR SEQ ID NO:8:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

Pro Val Pro Pro
    1

( 2 ) INFORMATION FOR SEQ ID NO:9:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

Ala Pro Val Pro Pro
    1               5

ANGIOTENSIN CONVERTING ENZYME INHIBITOR AND METHOD FOR PREPARING SAME

This is a continuation of application Ser. No. 08/090,530, filed Jul. 12, 1993 now abandoned.

BACKGROUND OF THE INVENTION

This invention relates to an angiotensin converting enzyme inhibitor consisting of a peptide having a specified number of amino acid residues containing Val-Pro-Pro as an effective constituent.

The angiotensin converting enzyme, referred to herein as ACE, is mainly present in lungs or vascular endothelial cells and acts on angiotensin I (Asp-Arg-Val-Tyr-Ile-His-Pro-Phe-His-Leu) decomposed by renin to isolate a dipeptide (His-Leu) from its C-terminal end to produce angiotensin II exhibiting a strong vasopressor action. Besides, the enzyme has an action of decomposing and inactivating bradykinin which decreases blood pressure. Since ACE not only produces a peptide which increases blood pressure (angiotensin II) but also decomposes and inactivates a peptide which decreases blood pressure (bradykinin), it exhibits the action of producing a rise in blood pressure. Such consideration has led to development of a variety of substances suppressing a rise in blood pressure by inhibiting such enzymatic activity.

A large number of ACE inhibiting natural and synthetic substances, inclusive of snake venom, have been reported to date. Such synthesized substance as captopril (D-2-methyl-3-mercaptopropanoyl-L-proline) has already been put to practical application as an orally administered vasodepressor. However, such pharmaceutical exhibits side effects in many cases and special attention needs be exercised in safety aspects. ACE inhibitors derived from foodstuff have been studied in many fields in expectation of a vasodepressor exhibiting low toxicity and high safety. For example, ACE inhibiting peptides produced by enzymatic hydrolysis of proteins, such as casein (Susumu Maruyama et al. A. B. C., 51(9), 2557-2561 (1987)), or fish meat protein (by Hiroyuki Ukeda, Nippon Nogei Kagaku Kaishi (Journal of Japan Society for Bioscience, Biotechnology, and Agrochemistry), 66(1), 25-29 (1992)), have been reported to date.

However, those substances supported by effective data obtained by oral administration are only few. Thus, a demand has been raised towards an effective vasodepressor which may be administered orally in a minor dosage with high safety.

Components of lactic acid bacteria have so far been known to exhibit ACE inhibiting capability or an action of producing decreased blood pressure, as reported by Sei Ito in "Medicine and Biology", 116(3), 159–161 (1988) and disclosed in Japanese Laid-Open Patent Publication No. 2-247127. Besides, a high molecular substance with a molecular weight of not less than 5,000 produced by removing microorganisms and casein from fermented milk, has been reported to exhibit an action of producing decreased blood pressure as disclosed in Japanese Laid-Open Patent Publication No. 61-53216. However, only a few reports have been made on ACE inhibitors other than those derived from microorganisms.

Meanwhile, tripeptide Val-Pro-Pro has been synthesized by Rao et al. as a partial constituent of collagen, and reported as being one of substances useful for explanation of racemization (Rao S. Rapaka, R. S. Bhatnagar and D. E. Nitecki, BIOPOLYMERS, 15, 317–324 (1976). However, this substance has not been known to exhibit ACE inhibiting activity. On the other hand, the tripeptide Val-Pro-Pro has been difficult to produce by chemical synthesis. Thus, a demand has been raised towards development of a method for producing such tripeptide easily on an industrial basis.

SUMMARY OF THE INVENTION

It is an object of the present invention to provide an ACE inhibitor which exhibits high safety and an effective ACE inhibitive activity through oral administration in a minor dosage and which may be employed as a pharmaceutical or physiologically functional foodstuff, and a method for producing such ACE inhibitor.

It is another object of the present invention to provide a method in which the ACE inhibitor may be produced easily and inexpensively.

The above and other objects of the present invention will become apparent from the following description.

According to the present invention, there is provided an angiotensin converting enzyme inhibitor containing as an effective constituent Val-Pro-Pro and containing 3 to 10 amino acid residues.

According to the present invention, there is also provided a method for producing the aforementioned angiotensin converting enzyme inhibitor comprising fermenting a foodstuff material containing Val-Pro-Pro as a constituent component with lactic acid bacteria.

PREFERRED EMBODIMENTS OF THE INVENTION

The present invention will be described in more detail hereinbelow.

In the ACE inhibitor of the present invention, it suffices if the peptide employed as its effective constituent is a Val-Pro-Pro containing peptide having 3 to 10 amino acid residues. It may also be such peptide to which pharmaceutically acceptable salts, such as hydrochlorates, sulfates, succinates, citrates or tartarates are added. The amino acid residues linked to Val-Pro-Pro are preferably linked to the N-terminal side. Besides, it is preferred that the number of the amino acid residues be small. Examples of the peptides preferably include peptides represented by amino acid sequences, such as Val-Pro-Pro SEQ ID NO: 1, Val-Val-Pro-Pro SEQ ID NO: 2, Val-Val-Val-Pro-Pro SEQ ID NO: 3, Pro-Val-Val-Val-Pro-Pro SEQ ID NO: 4, Leu-Thr-Gln-Thr-Pro-Val-Val-Val-Pro-Pro SEQ ID NO: 5, Leu-Val-Pro-Pro SEQ ID NO: 6, Phe-Leu-Val-Pro-Pro SEQ ID NO: 7, Pro-Val-Pro-Pro SEQ ID NO: 8 and Ala-Pro-Val-Pro-Pro SEQ ID NO: 9, and salt adducts thereof. These peptides or salt adducts thereof may be used alone or in combination.

The Val-Pro-Pro containing peptide with 3 to 10 amino acid residues employed as the ACE inhibitor according to the present invention, may be produced not only by the method of the present invention as later explained, but also by a method of enzymatic hydrolysis of milk protein components, such as whole or defatted animal milk or casein, corn, corn protein, wheat, wheat protein, soybean, defatted soybean or soybean protein, or a method of conventional organochemical synthesis.

It suffices if the ACE inhibitor of the present invention contains the aforementioned particular peptide. Besides, it may also be admixed with pharmaceutically acceptable additives, foodstuffs or beverage, and orally administered in a solid or liquid form. Although its dosage is variable with the progress of the symptoms or depending on whether it is used for therapy or prevention, it may be administered in an amount calculated as the aforementioned particular Val-Pro-Pro containing peptide with 3 to 10 amino acid residues which is preferably equal to 0.1 mg to 100 mg a day and more preferably equal to 1 to 30 mg a day, if the inhibitor is administered for therapy or prevention for adults.

With the method for producing the ACE inhibitor according to the present invention, it may be produced by fermentation of a foodstuff material containing the Val-Pro-Pro containing peptide, referred to herein as a VPP foodstuff material, with lactic acid bacteria.

The VPP foodstuff material may preferably be enumerated by, for example milk protein components, such as whole or defatted animal milk or milk casein, corn, corn protein, wheat, wheat protein, soybean, defatted soybean or soybean protein. The aforementioned lactic acid bacterial may preferably be enumerated by, for example lactic acid bacteria belonging to genus Lactobacillus, such as *Lactobacillus helveticus, Lactobacillus delbreukii* subsp. *bulgaricus*, etc., lactic acid bacteria belonging to genus Lactococcus, such as *Lactococcus lactis*, lactic acid bacteria belonging to genus Streptococcus, such as *Streptococcus thermophilus*, lactic acid bacteria belonging to genus Leuconostoc, such as *Leuconostoc lactis*, and lactic acid bacteria belonging to genus Bifidobacterium, such as *Bifidobacterium longum* or *Bifidobacterium breve*. The lactic acid bacteria may be used as a mixture with other microorganisms, e.g. yeasts. These yeasts may preferably be enumerated by, for example yeast belonging to the genus Saccharomyces, such as *Saccharomyces cerevisiae*, yeast belonging to the genus Candida, such as *Candida utilis*, yeast belonging to the genus Kluyveromyces, such as *Kluyveromyces marxianus* var *lactis*, and mixtures thereof.

In the method of the present invention, the VPP foodstuff material is fermented by lactic acid bacteria under operating conditions which may be varied depending on the types and/or the combination of the lactic acid bacteria. Preferably, however, the VPP foodstuff material is dissolved in water to give a solution, which is then admixed with lactic acid bacteria and cultivated by way of fermentation. Preferably, the cultivation temperature and the cultivation time are 25° to 45° C. and 3 to 72 hours, respectively. Above all, for achieving an effective action of the lactic acid bacteria, the pH value at the start of fermentation by cultivation is preferably adjusted to 6 to 7. The end point of fermentation by cultivation may, for example be set to a time point when the number of lactic acid bacteria becomes equal to not less than $10^7$/ml or when the pH value becomes equal to 5.5 or lower. Otherwise, pH of the solution may be maintained at neutral pH by the addition of alkali substances such as NaOH or KOH in the course of the fermentation. The proportion of the lactic acid bacteria for cultivation is preferably approximately equal to $5 \times 10^6$, in terms of the number of bacteria, to 1 ml of the solution of the VPP foodstuff material at the start of the fermentation. It is also possible to carry out the cultivation in a plurality of number of times of partial cultivating operations.

The fermented milk produced by the method of the present invention may directly be employed as an effective constituent of the ACE inhibitor. However, it may also be purified by column chromatography or any of a variety of biochemical methods for eliminating components other than the effective components, such as bitter-tasting components. The Val-Pro-Pro containing peptide, as the aforementioned effective component, contained in the resulting fermented milk is present in an amount of 1 to 4 mg per 100 ml of the fermented milk. Therefore, If the fermented milk is directly employed as the ACE inhibitor of the present invention, it is administered in an amount of 10 ml to 1000 ml a day and preferably in an amount of 50 to 300 ml a day for adults.

The ACE inhibitor of the present invention, containing the specified peptide as the effective component, exhibits superior ACE inhibiting activities through oral administration in only minor quantities. Besides, the method of the present invention is industrially highly effective because the ACE inhibitor may thereby be produced easily and inexpensively.

EXAMPLES OF THE INVENTION

The present invention will be explained with reference to Examples which are given only by way of illustration.

Example 1

Preparation of Fermented Milk a 9 g of defatted skim milk powders were dissolved in 100 g of water. After pasteurization at 115° C. for 20 minutes, the solution was cooled to fermentation temperature, and inoculated with *Lactobacillus helveticus* JCM-1004 using a platinum loop wire. A primary starter (pH, 3.5), containing $5 \times 10^8$ lactic acid bacteria per ml of the solution, was prepared by cultivation at 37° C. for 24 hours. 180 g of defatted skim milk powders were dissolved in 2 kg of water to give an aqueous solution, which was then pasteurized at an elevated temperature of 90° C. After cooled to fermentation temperature, the pasteurized solution was inoculated with the above-mentioned primary starter. Cultivation was continued at 37° C. for 24 hours to give a secondary starter. 4.5 kg of defatted skim milk powders were dissolved in 50 kg of water and pasteurized at an elevated temperature of 90° C. The resulting solution was cooled to fermentation temperature and inoculated with the aforementioned secondary starter. Cultivation was continued at 37° C. for 24 hours to produce approximately 56 kg of fermented milk a.

Quantitation of Peptide b (Val-Pro-Pro) Contained in Fermented Milk 5 ml of the aforementioned fermented milk a were centrifuged at 10,000 rpm for five minutes, and a resulting supernatant was charged into a column containing 1 g of "AMBERLITE XAD-7", a trade name of a resin manufactured by ROHM & HAAS CO. The content of the column was washed with 5 ml of water and mixed with a non-absorbed fraction. The resulting mixture was charged into a combined column made up of two columns "SEP-PAK C18", a trade name of a column manufactured by WATERS INC. and washed with 5 ml of distilled water. After elution of the adsorbed fraction with 5 ml of methanol, the resulting product was concentrated by a centrifugal concentrator ("MODEL CC-101", TOMY SEIKO CO., LTD.) and freeze-dried under reduced pressure. The resulting dried mass was dissolved in a 0.05 mol of an ammonium acetate buffer (pH 6.89) and subjected to separation by HPLC using a column "GS320HQ", a trade name of the product manufactured by ASAHI CHEMICAL INDUSTRY CO., LTD. equilibrated by the same buffer. The peptide eluted at a flow rate of 0.6 ml/min. The peak with the elution time of 14.5 to 15.5 minutes was fractionated and quantitated under the following conditions:

Conditions of Quantitation

Column: μ BONDASPHERE 5 μC18, manufactured by WATERS INC.

Conditions of Elution: Solution S, a 0.1 wt % aqueous solution of TFA; solution B, acetonitrile containing 0.1 wt % of TFA Gradient elution (B/A+B)×100(%): 0% to 40% (60 minutes)

Flow rate, 1 ml/min; Detection: absorption of ultraviolet rays at 215 nm.

Using the resulting peptide as a standard, the weight of the peptide b contained in the filtrate was calculated. It was found that 1.65 g of peptide b was contained in 56 kg of the fermented milk a.

Preparation of Peptide b

For purifying the peptide contained in the resulting fermented milk a, the following purification process was carried out.

6 liter of the fermented milk a were adjusted with a 10N NaOH solution to a pH value in the vicinity of 7.3, and admixed with about 1 liter of a resin manufactured under the trade name of "AMBERLITE XAD-2" by ROHM & HAAS CO. and subsequently with distilled water to give a total volume equal to about 20 liter. The resulting product was agitated for 90 minutes and filtered through a bleached cloth to recover the resin. After washing with 20 liter of distilled water, the resin was added to 1 liter of methanol and agitated for 30 minutes. The resulting product was filtered using a nylon wool of a 200 mesh size and subsequently filtered under reduced pressure using a hard filter paper. The resulting filtrate was concentrated at 55° C. under reduced pressure by an evaporator to produce 200 ml of a concentrated liquid, which then was admixed with 250 ml of a resin manufactured by ROHM & HAAS CO. under the trade name of "AMBERLITE IRA-400" (OH-type) and agitated with a spatula for eliminating the yellowish tint of the liquid. The resulting liquid was filtered under reduced pressure using a hard filter paper and the resulting filtrate was adjusted to pH 7 using a 1N hydrochloric acid solution and freeze-dried. The resulting dried product was dissolved in a small quantity of distilled water and charged into a column manufactured by PHARMACIA FINE CHEMICALS CO. under the trade name of "SEPHADEX G-25". The resulting product was eluted with distilled water and an active fraction was collected and freeze-dried to produce 50 mg of powders. The dried powders were dissolved in a 0.05M acetic acid buffer (pH, 4.5) and charged into a column manufactured by PHARMACIA FINE CHEMICALS CO. under the trade name of "SP-SEPHADEX C-25" equilibrated with the same buffer for elution by the buffer. The active fraction was collected and freeze-dried. The resulting freeze-dried mass was dissolved in a minor quantity of a 0.1 wt % aqueous solution of TFA and subjected to separation using high speed high performance liquid chromatography (HPLC). For HPLC, a reverse phase column, manufactured by YAMAMURA CHEMICAL LAB. CO., LTD. under the trade name of "YMS-PACK A-302" was used, and separation was carried out at a linear gradient of 0 to 40% (60 minutes), using 2-propanol/acetonitrile containing 0.1 wt % of TFA at a ratio of 7:3 as a solvent, to produce 1 mg of peptide b having a sole peak and exhibiting ACE inhibiting activity.

The resulting peptide b was analyzed in accordance with the following methods.

Amino Acid Composition

1 μg of the resulting peptide b was dissolved in 6N constant-boiling hydrochloric acid and hydrolyzed in vacuum at 110° C. for 24 hours. The resulting product was analyzed as to its composition by a ninhydrin coloration method using an analyzer manufactured by HITACHI LTD. under the trade name of "HITACHI L-8500 TYPE AMINO ACID ANALYZER". The Val-Pro molar ratio was found to be 1.00:2.08.

Amino Acid Sequence

The amino acid sequence at the N-terminal was analyzed and measured using an analyzer manufactured by SHIMADZU CO. under the trade name of "SHIMADZU PROTEIN SEQUENCER PSQ-1". It was found that the N-terminal amino acid sequence was Val-Pro-Pro.

Measurement of ACE Inhibiting Activity

The ACE inhibiting activity was measured in accordance with the method by Cushman and Cheung as described in "D. W. Cushman and H. S. Cheung, Biochem. Pharmacol., 20 1637 (1971).

The samples of peptide b, prepared as above, were adjusted to concentrations of 12.5, 25.0, 50.0, 100 and 200 μg/ml, using a 0.1M boric acid buffer containing 0.3M Nacl, pH 8.3, and charged in amounts of 0.08 ml in test tubes. 0.2 ml of hippuryl histidyl leucine (Hip-His-Leu, manufactured by SIGMA CHEMICAL CO.), adjusted to 5 mM with a 0.1M boric acid buffer containing 0.3M NaCl, pH 8.3, and 0.02 ml of an aqueous enzyme solution (ACE, 0.1 u/ml, manufactured by SIGMA CHEMICAL CO.) were added in this order as a substrate to the contents of each test tube, and reaction was carried out at 37° C. for 30 minutes. 0.25 ml of 1N hydrochloric acid was subsequently added to the contents of each test tube. After termination of the reaction, 1.7 ml of ethyl acetate was added to the contents of each tube, and agitation was continued for 20 seconds. After centrifugal separation at 3000 rpm for 10 minutes, and recovery of 1.4 ml of an ethyl acetate layer, the solvent was removed by heating at 120° for 40 minutes. After removing the solvent and adding 1 ml of distilled water, the absorption at 228 nm of the extracted hippuric acid was measured and adopted as the ACE inhibiting activity. The inhibiting ratio was calculated by the following equation:

$$\text{Inhibiting Percentage} = [(A-B)/(A-C)] \times 100(\%)$$

where A is the absorbance at 228 nm of hippuric acid free of sample (peptide b), B is the absorbance at 228 nm of hippuric acid admixed with sample (peptide b), and C is the absorbance at 228 nm of hippuric acid free of enzyme and sample (peptide b).

The concentration of the inhibitor at 50% inhibiting percent ($IC_{50}$) was then found. The value of $IC_{50}$ for the peptide b produced was 14 μM.

Measurement of the Vasodepressor Action on Oral Administration to Rat

The vasodepressor action of the resulting fermented milk a and peptide b was measured by the following method.

Spontaneously hypertensive rats (SHR) (four in each group), each 26 weeks of age, furnished by CHARLES RIBER JAPAN INC., were tamed and kept, by being fed freely with water and feed manufactured by CLEA JAPAN INC. under the trade name of "CE-2", in an animal room maintained at a temperature of 23°±2° C. and a humidity of 55±5%. To SHR, not fed overnight from the day preceding the test, physiological saline, fermented milk a and peptide b dissolved in physiological saline were orally administered forcibly, using a stomachic sonde, in amounts of 2 ml per rat, and 150 μg per rat, respectively. Blood pressure of the rats was measured directly before administration and in four and eight hours after administration. Blood pressure measurement was made by a tail-cuff method with programmed electrosphygomano meter manufactured by NARCO BIO-SYSTEMS CO., LTD. under the trade name of "PE-300". The differences in blood pressure between the blood pressure directly before administration and that after 4 hours and that after 8 hours are shown in Table 1.

TABLE 1

| Sample | After 4 hrs. | After 8 hrs. |
| --- | --- | --- |
| Physiological Saline (control) | −0.5 mmHg | −2.4 mmHg |
| Fermented milk a | −37.0 mmHg | −31.5 mmHg |
| Peptide b | −32.0 mmHg | −26.5 mmHg |

Example 2

To 55 kg of the fermented milk a, produced in Example 1, 5 kg of a resin manufactured by ROHM & HAAS CO. under the trade name of "AMBERLITE XAD-2" were added. The resulting mixture was agitated for 90 minutes at room temperature and filtered by a bleached cloth to recover the resin. After washing with 10 liter of water, the resin was added to 2.5 liter of ethanol and agitated for 30 minutes. The resulting product was filtered using a 200 mesh size nylon wool cloth and further filtered under reduced pressure using a hard filter paper. The resulting filtrate was concentrated under reduced pressure at 55° C. by an evaporator and freeze-dried to give about 3.1 g of peptide powders. The peptide powders were quantitated by a method similar to that used for quantitation of the peptide b contained in the fermented milk a of Example 1, and were found to contain 0.4 g of peptide b.

40.0 parts by weight of lactose, 34.8 parts by weight of sucrose, 5.0 parts by weight of tragacanth gum powders and 0.2 part by weight of peppermint oil were mixed together. A solution in which 20.0 parts by weight of the peptide powders were dissolved in 20.0 parts by weight of distilled water was added to the resulting mixture and kneaded thoroughly. The resulting kneaded product was spread on a glass plate sprinkled with starch to form a sheet, which was subsequently punched by a matrix and dried to produce lozenges each weighing 1 g.

Example 3

Synthesis of Phe-Leu-Val-Pro-Pro 0.01 mmol of Fmoc-Leu resin and each 0.1 mmol of Fmoc-Phe, Fmoc-Pro, Fmoc-Pro and Fmoc-Val were charged into a peptide synthesizer manufactured by SHIMADZU CO. under the trade name of "PSSM8", and an Fmoc-Phe-Leu-Val-Pro-Pro-Phe resin was synthesized, using a condensation agent PyBOP (benzotriazol-1-yl-oxy-tris (pyrrolidino) phosphonium hexafluoro phosphate). The resulting resin was washed five times with 1 ml of methanol and twice with 1 ml of t-butylmethyl ether and dried.

After a step of desorption from the resin by a mixed solution of anisole-1, 2-ethanedithiol-TFA (5:1:94), the peptide was washed three times with anhydrous ether and dissolved in 0.01M HCl. The resulting solution was freeze-dried to produce 2.65 ml of white-tinted powders.

These powders were dissolved in 1 ml of 0.1M tris-HCl containing 0.9M KCl (pH 7.5). To the resulting solution there were added 6 milliunits of "CARBOXY-PEPTIDASE A", derived from bovine pancreas, manufactured by SIGMA CHEMICAL CO. Reaction was continued at 37° C. for 24 hours for desorbing amino acids Phe and Leu from the C-terminal side. After completion of the reaction, the peptide showed by HPLC a sole peak at a position corresponding to the elution time of 35.2 minutes. Elution by HPLC was carried out in the same way as in Example 1. The peak was fractionated and, after centrifugal concentration under reduced pressure and freeze-drying, 891 mg of white-tinted powders were produced.

Amino Acid Composition

A part of the peptide was dissolved in constant-boiling 6N hydrochloric acid and hydrolyzed at 110° C. for 24 hours under vacuum. The resulting product was analyzed as to its composition, using an amino acid analyzer operating by OPA coloration method, manufactured by JAPAN SPECTROSCOPIC CO., LTD. under the trade name of "PU 980". The peptide was found to be composed of Val:Pro:Leu:-Phe=1.00:2.00:1.06:1.08.

Amino Acid Sequence

As a result of analyses by an analyzer manufactured by SHIMADZU CO. under the trade name of "SHIMAZU PROTEIN SEQUENCER PSQ-1", the peptide was found to have an amino acid sequence of Phe-Leu-Val-Pro-Pro.

Chemical Synthesis of Other Val-Pro-Pro Containing Peptides

Val-Pro-Pro, Val-Val-Pro-Pro, Val-Val-Val-Pro-Pro, Pro-Val-Val-Val-Pro-Pro, Leu-Thr-Gln-Thr-Pro-Val-Val-Val-Pro-Pro, Leu-Val-Pro-Pro, Pro-Val-Pro-Pro and Ala-Pro-Val-Pro-Pro were synthesized in accordance with synthesis of Phe-Leu-Val-Pro-Pro mentioned above.

Measurement of ACE Inhibiting Activities

For each of the peptides synthesized by the above-mentioned method of chemical synthesis, the values of $IC_{50}$ were measured in the same way as in measuring the ACE inhibiting activities in Example 1. The results are shown in Table 2.

TABLE 2

| Synthesized Peptides | $IC_{50}$ (μM) |
| --- | --- |
| Phe—Leu—Val—Pro—Pro | 12 |
| Val—Pro—Pro | 9 |
| Val—Val—Pro—Pro | 285 |
| Val—Val—Val—Pro—Pro | 873 |
| Pro—Val—Val—Val—Pro—Pro | 117 |
| Leu—Thr—Gln—Thr—Pro—Val—Val—Val—Pro—Pro | 160 |
| Leu—Val—Pro—Pro | 125 |
| Pro—Val—Pro—Pro | 181 |
| Ala—Pro—Val—Pro—Pro | 627 |

Although the present invention has been described with reference to the preferred examples, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

1. A method of treating elevated blood pressure in a mammal in need of such treatment which comprises administering to said mammal an angiotensin converting enzyme inhibitor having as an effective constituent a member selected from the group consisting of Val-Pro-Pro, Val-Val-Pro-Pro, Val-Val-Val-Pro-Pro, Pro-Val-Val-Val-Pro-Pro, Leu-Thr-Gln-Thr-Pro-Val-Val-Pro-Pro, Leu-Val-Pro-Pro, Phe-Leu-Val-Pro-Pro, Pro-Val-Pro-Pro, Ala-Pro-Val-Pro-Pro, salt adducts thereof, and mixtures thereof.

2. The method as claimed in claim 1 wherein the salt is selected from the group consisting of hydrochlorate, sulfate, succinate, citrate and tartarate.

* * * * *

UNITED STATES PATENT AND TRADEMARK OFFICE
CERTIFICATE OF CORRECTION

PATENT NO.   :   5,449,661
DATED        :   September 12, 1995
INVENTOR(S)  :   Yasunori Nakamura et al.

It is certified that errors appear in the above-identified patent and that said Letters Patent is hereby corrected as shown below:

The Sequence in Claim 1, column 13, lines 5-6 should read

"Leu-Thr-Gln-Thr-Pro-Val-Val-Val-Pro-Pro".

Signed and Sealed this

Twenty-fourth Day of October, 2000

Attest:

Q. TODD DICKINSON

*Attesting Officer*    *Director of Patents and Trademarks*